United States Patent [19]

Joseph-Nathan et al.

[11] Patent Number: 4,922,032

[45] Date of Patent: May 1, 1990

[54] PROCESS FOR THE PREPARATION OF OPTICALLY ACTIVE 2-METHYL-1,2-HEXANEDIOLS

[75] Inventors: Pedro Joseph-Nathan; Humberto Cervantes-Cuevas, both of Mexico City, Mexico

[73] Assignee: Centro De Investigacion Y De Estudios Avanzados Del Instituto Politecnico Nacional, Mexico City, Mexico

[21] Appl. No.: 343,272

[22] Filed: Apr. 26, 1989

[51] Int. Cl.[5] .................... C07C 29/136; C07C 31/20
[52] U.S. Cl. .................................. 568/862; 568/868; 568/872
[58] Field of Search ......................... 568/862

[56] References Cited

U.S. PATENT DOCUMENTS 4,633,025 12/1985 Corey .................................. 568/866
4,668,822 5/1987 Corey .................................. 562/579

OTHER PUBLICATIONS

Lynch et al., (1984) J. Amer. Chem. Soc. 106: 2943–48.
Eliel et al. (1987) Org. Synth. 65: 215–222.
Collins (1986) J. Med. Chem. 29: 437–443.

Primary Examiner—J. E. Evans
Attorney, Agent, or Firm—Fleit, Jacobson, Cohn, Price, Holman & Stern

[57] ABSTRACT

Disclosed is the preparation of both optically active stereoisomers of 2-methyl-1,2-hexanediol, which are useful intermediates for the syntheses of several prostaglandins for peptic ulcer therapy.

10 Claims, No Drawings

PROCESS FOR THE PREPARATION OF OPTICALLY ACTIVE 2-METHYL-1,2-HEXANEDIOLS

BACKGROUND AND PRIOR ART

The compound 2-methyl-1,2-hexanediol characterized by the structural formula:

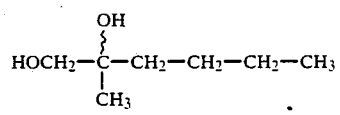

is an intermediate in the syntheses of several prostaglandins that are useful for peptic ulcer therapy.

In this respect Collins (J. Medic. Chem. 29[4], 437 [1986]) states that four synthetic prostaglandins which contain a 4-hydroxy-4-methyl-1(E)-octenyl group as the substituent at position 3 of the cyclopentanone are in clinical use for peptic ulcer therapy.

The first of these four prostaglandins is (±)-4α-hydroxy-3β(4RS)-[4-hydroxy-4-methyl-1(E)-octenyl]-2α-[6-carbomethoxyhexanyl]-cyclopentanone characterized by the structural formula:

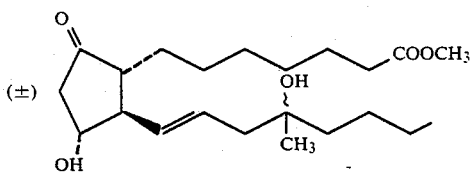

The second of these four prostaglandins is 4α-hydroxy-3β-(4RS)--[4-hydroxy-4-methyl-1(E)-octenyl]-2α-[7-hydroxyheptanyl]cyclopentanone characterized by the structure formula:

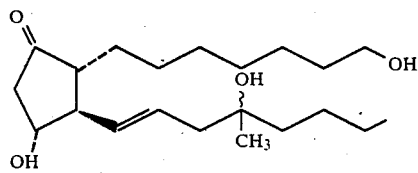

The third of these four prostaglandins is (±)-4α-hydroxy-3β-(4RS)-[4-hydroxy-4-methyl-1(E)-octenyl]-2α-[7-oxo-8-hydroxyoctanyl]cyclopentanone characterized by the structural formula:

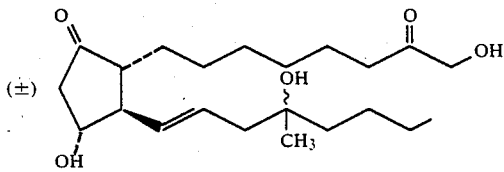

The fourth of these four prostaglandins is (±)-4α-hydroxy-3β-(4RS)-[4-hydroxy-4-methyl-1(E)-octenyl]-2α-[6-carbomethoxy-3(Z)-hexenyl]cyclopentanone characterized by the structural formula:

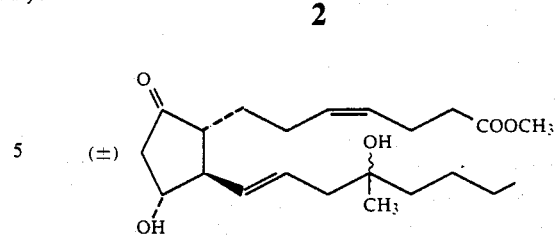

Collins (J. Medic. Chem. 29[4], 437 [1986]) also states that the four synthetic prostaglandins whose structural formulae are given above are in clinical use as mixtures of stereoisomers since the preparation of a single stereoisomer is complicated by the fact that chromatographic separation of prostaglandin mixtures of stereoisomers in the 16-methyl-16-hydroxy series is difficult and cannot be done at a practical scale.

However, it is well known in the art that the most active synthetic prostaglandin analogues are those that have a specific stereochemistry at each quiral center.

Collins (J. Medic. Chem. 29[4], 437 [1986]) further states that the major process for the preparation of the four compounds whose structural formulae are given above consists of a 1,4 conjugate addition of an organometallic compound characterized by the structural formula:

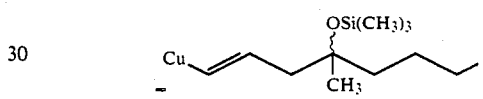

to a cyclopentenone of the general formula:

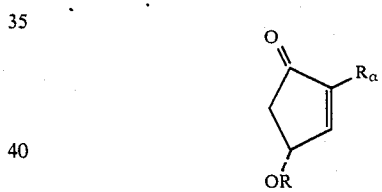

where R is a protecting group and $R_\alpha$ is the desired "alpha chain", and that therefore the effective ways in which a single stereoisomer of these prostaglandins can be obtained, is by resolution of both the desired substituted cyclopentenone and of the "omega chain", which means the precursor of the organometallic compound whose structural formula is given above, or by a combination of resolution of stereoisomers and synthetic asymmetric induction.

Collins continues to state that although reasonably efficient methods have been developed to resolve the desired substituted cyclopentenones, no good method has been found to resolve 4-hydroxy-4-methyl-1-octyne, characterized by the structural formula:

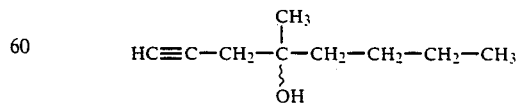

which is then converted into the organometallic compound whose structural formula is given above.

In turn, 4-hydroxy-4-methyl-1-octyne is prepared from 2-methyl-1,2-hexanediol whose structural formula is given above.

Thus, development of a convenient method to prepare individual stereoisomers of 2-methyl-1,2-hexanediol will lead to a substantial reduction of the clinical doses of the four synthetic prostaglandins whose structural formulae are given above.

Various methods have been developed for the preparation of a given individual stereoisomer of 2-methyl-1,2-hexanediol. Most of these methods and their disadvantages have been summarized by Corey (U.S. Pat. No. 4,633,025 issued Dec. 30, 1986, and U.S. Pat. No. 4,668,822 issued May 26, 1987) who also teaches the preparation of individual stereoisomers of 2-methyl-1,2-hexanediol and of 2-hydroxy-2-methylhexanoic acid. The latter, by reduction, also provides 2-methyl-1,2-hexanediol. The disadvantage of these methods of Corey is that long multi-step sequences of reactions are necessary for the preparation of the desired stereoisomers of 2-methyl-1,2-hexanediol.

The invention described herein teaches short methodology for the preparation of (+)-R-2-methyl-1,2-hexanediol and of (−)-S-2-methyl-1, 2-hexanediol. These compounds can subsequently be used for the preparation of individual stereoisomers of certain optically active prostaglandins such as those whose structural formulae are given above.

SUMMARY OF THE INVENTION

The present invention involves a short synthetic process for the obtention of each of the two optically active steroisomers of 2-methyl-1,2-hexanediol which are intermediates in the syntheses of several prostaglandins detailed in the background and prior art section that are useful for peptic ulcer therapy.

One of the two optically active stereoisomers is (+)-R-2-methyl-1, 2-hexanediol characterized by the structural Formula I:

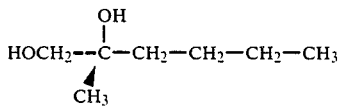

The process for preparing the compound having Formula I from 2-hexanone characterized by the structural Formula II:

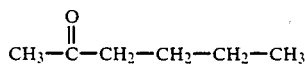

comprises the following steps:

(a) reacting the compound having Formula II with a compound having Formula III:

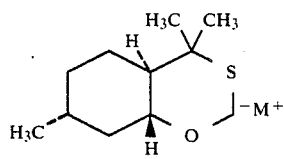

where M+ is an alkali metal cation and acidifying the solution to produce the compound having Formula IV:

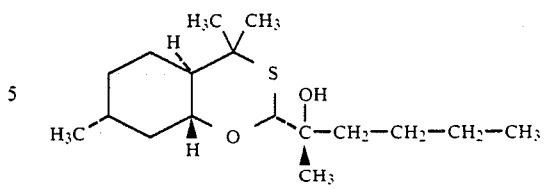

(b) separating the compound having Formula IV from the reaction mass;

(c) reacting the compound having Formula IV with an oxidizing agent in the presence of a suitable inorganic salt to produce the compound having Formula V:

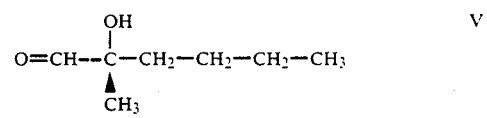

(d) reacting the compound having Formula V with a reducing agent to provide the desired product having Formula I above; and (e) isolating the desired product having Formula I above from the reaction mass.

The other of the two optically active stereoisomers is (−)-S-2-methyl-1,2-hexanediol characterized by the structural Formula VI:

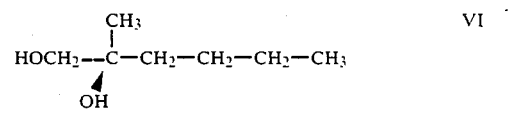

The process for preparing the compound having Formula VI from 2-hexanone having Formula II above comprises the following steps:

(a) reacting the compound having Formula II above with the compound having Formula III above and acidifying the solution to produce the compound having Formula VII:

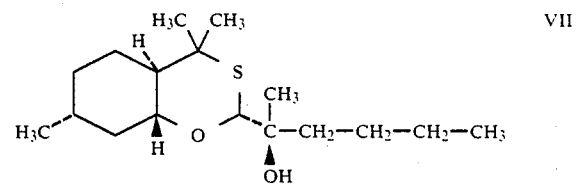

(b) separating the compound having Formula VII from the reaction mass;

(c) reacting the compound having Formula VII with an oxidizing agent in the presence of a suitable inorganic salt to produce the compound having Formula VIII:

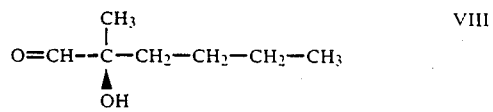

(d) reacting the compound having Formula VIII with a reducing agent to provide the desired product having Formula VI above; and (e) isolating the desired product having Formula VI above from the reaction mass.

DETAILED DESCRIPTION OF THE INVENTION

The process for preparing the compound having Formula I:

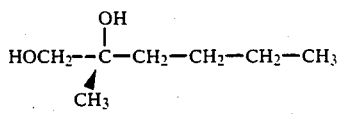

begins by reacting the compound having Formula II:

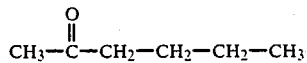

with a compound having Formula III:

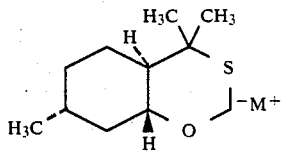

where M+ is an alkali metal cation to produce the compound having Formula IV:

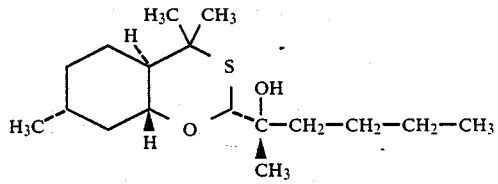

The compound having Formula IV can be prepared as described in Example I below.

The alkali metal base used for the in situ preparation of Compound III may be butyllithium, sec-butyllithium, tert-butyllithium, methyllithium, or the like. The reaction may be performed in a suitable solvent such as tetrahydrofuran, diethyl ether, hexane, dioxane, or the like, or the solvent may be a mixture of the above mentioned compounds.

The molar ratios of the alkali metal base to the precursor of Compound III preferably range from about 1:1 to 11:10, respectively, with the latter ratio preferred. The preferred alkali metal base is butyllithium and the preferred solvent is a mixture of hexane and tetra hydrofuran. The reaction takes place in the temperature range of from about −80° C. to 0° C. but it is preferred to maintain initially the temperature around −78° C. and then slowly warm the reaction mixture to 0° C.

Once the compound having Formula III is generated, it is immediately reacted with the compound having Formula 11. In this process a carbon-oxygen double bond is transformed into a carbon-oxygen single bond a carbon-carbon bond is formed and the negative charge at the oxygen atom is neutralized in the solution by the alkali metal cation. Therefore the reaction is initiated at a temperature near −78° C. and after sometime, in order to drive the reaction to completion, the reaction mixture is allowed to slowly warm up to the room temperature. The molar ratios of Compound II to the precursor of Compound III range from about 11:10 to 1:1, respectively, with the latter ratio preferred and the preferred solvent for the reaction is the same as that used for the generation of Compound III. The solution is then acidified with aqueous ammonium chloride and the compound having Formula IV is then isolated from the reaction mass by convenient means such as extraction followed by column chromatography.

The compound having Formula IV above is then converted into the compound having Formula V:

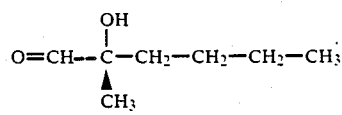

In this process an oxathiane group is oxidatively cleaved to produce an aldehyde group and as a side product (3aR,6R,7aR)-hexahydro-3,3,6-trimethyl-2-oxide-3H-1,2-benzoxathiole is formed. The latter can be reconverted into the precursor of Compound III as describe by LYNCH and BLIBL, J. Amer. Chem. Soc. 106[10], 2944[1984].

The conversion of the oxathiane group of Compound IV into the aldehyde group of Compound V is performed with an oxidizing agent. The oxidizing agent may be N-chlorosuccinimide, N-bromosuccinimide, or the like. The reaction yields are improved by the use of a suitable inorganic salt which contributes to weaken the nitrogen-halogen bond of the oxidizing agent. The inorganic salt may be silver nitrate, cadmium nitrate, cupric chloride, mercuric chloride, silver perchlorate, or the like. The reaction may be performed in a suitable solvent such as aqueous acetonitrile, aqueous acetone, aqueous tetrahydrofuran, aqueous methanol, aqueous ethanol, or the like.

The molar ratios of oxidizing agent to compound IV preferably range from about 2:1 to 9:4, respectively, with the latter ratio preferred and the molar ratios of the inorganic salt to the oxidizing agent preferably range from about 1:1 to 11:10, respectively, with the latter ratio preferred. The preferred oxidizing agent is N-chlorosuccinimide, the preferred inorganic salt is silver nitrate and the preferred solvent is aqueous acetonitrile. The reaction takes place in the temperature range of from about −10° C. to 0° C. but it is preferred to have the temperature near −5° C.

The compound having Formula V is immediately converted into the desired compound having Formula I above. In this process an aldehyde group is reduced to produce a primary alcohol group.

The conversion of the aldehyde group of Compound V into the primary alcohol group of compound I is performed with an excess of a reducing agent such as sodium borohydride, lithium borohydride, or the like. The reaction may be performed in the same solvent as the conversion of the compound having Formula IV above into the compound having Formula V above.

The preferred reducing agent is sodium borohydride. The reaction takes place in the temperature range of from about 0° C. to 30° C. but it is preferred to have the temperature near 25° C.

The desired compound having Formula I above is then isolated from the reaction mass by convenient means such as extraction followed by column chromatography.

Our preferred mode for the conversion of the compound having Formula IV into the desired compound having Formula I is further illustrated in Example 2, below.

In a similar manner, the process for preparing the compound having Formula VI:

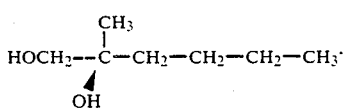

begins by reacting the compound having Formula II above with a compound having Formula III above to produce the compound having Formula VII:

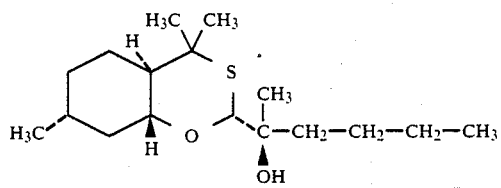

The considerations and reaction conditions for the conversion of the compound having Formula II into the compound having Formula VII are the same as those indicated above for the conversion of the compound having Formula 11 into the compound having Formula IV.

Our preferred method for the conversion of the compound having Formula II into the compound having Formula VII is further illustrated in Example 3, below.

By comparing Examples 1 and 3, it will be seen that Examples 1 and 3 are the same reaction with the exception that in Example 1, 5 liters from the chromatography column were eluted to isolate the Compound IV, while in Example 3 these 5 liters were discarded and then further elution from the chromatography column permitted the isolation of Compound VII.

The compound having Formula VII is then isolated from the reaction mass by convenient means and is converted into the compound having Formula VIII:

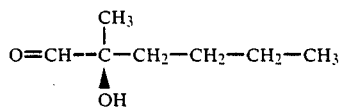

The considerations and reaction conditions for the conversion of the compound having Formula VII into the compound having Formula VIII are the same as those indicated above for the conversion of the compound having Formula IV into the compound having Formula V.

The compound having Formula VIII is immediately converted into the desired compound having Formula VI.

The considerations and reaction conditions for the conversion of the compound having Formula VIII into the desired compound having Formula VI are the same as those indicated above for the conversion of the compound having Formula V into the compound having Formula I.

Our preferred mode for the conversion of the compound having Formula VII into the desired compound having Formula VI is further illustrated in Example 4, below.

The preparation of the compounds of the present invention is further illustrated by the following examples:

EXAMPLE 1

Preparation of (2R,4aR,7R,8aR)-hexahydro-2[(2R)-2-hydroxy-2-hexanyl]-4,4,7-trimethyl-1H-1,3-benzoxathiin (Compound IV)

A vigorously stirred solution of (4aR,7R,8aR)-hexahydro-4,4,7-trimethyl-4H-1,3-benzoxathiin (9 g, 0.045 mole, prepared as described by ELIEL et al. Org. Synth. 65, 215 [1987]) in 130 ml of anhydrous tetrahydrofuran was cooled to $-78°$ C. under an ar8on atmosphere and butyllithium (3.168 g, 0.0195 mole) dissolved in 32 ml of hexane was added dropwise over a period of 15 minutes. The solution was further stirred for additional 15 minutes. The temperature of the solution was allowed to slowly reach $0°$ C. and further stirred for 15 minutes. The solution was cooled again to $-78°$ C. under the argon atmosphere, the stirring was continued and 2-hexanone (4.5 g, 0.045 mole) dissolved in 25 ml of anhydrous tetrahydrofuran was added dropwise over a period of 20 minutes. The solution was further stirred for additional 4 hours. The temperature of the solution was allowed to slowly reach the room temperature, 10 ml of water were added dropwise over a period of 10 minutes and then 15 ml of a saturated solution of ammonium chloride in water were added at once. The reaction mixture was S partitioned between diethyl ether and water. The ether portion was washed with brine, dried over anhydrous $Na_2SO_4$ which was then removed by filtration, and evaporated to leave 13.1 g of a thick syrup. This thick syrup was dissolved in 10 ml of hexane-ethyl acetate (9:1 v:v) solvent and chromatographed on 1000 g of silica gel (230-400 mesh ASTM). The 5 liters of hexane-ethyl acetate that were eluted, were evaporated in vacuo to leave a viscous colorless liquid residue. This liquid was distilled at reduced pressure. The fraction distilling at $95°-97°$ C. and 0.05 Torr was collected yielding 6.2 g (45.9%) of the title compound, which shows $[\alpha]_{365}=-28.91°$ (C=1.61 in $CHCl_3$). Anal. Calcd. for $C_{17}H_{32}O_2S$: C,67.96; H,10.74; O,10.65; S,10.65, Found: C,68.20; H,10.63; O,10.47; S,10.56.

EXAMPLE 2

Preparation of (+)-R-2-methyl-1,2-hexanediol (Compound 1)

A solution of N-chlorosuccinimide (1 g, 0.00749 mole) in 50 ml of acetonitrile was mixed with a solution of silver nitrate (1.33 g, 0.00782 mole) in 12.5 ml of water. The resulting solution was cooled to $-5°$ C. and a solution of Compound IV, prepared above, (1 g, 0.00333 mole) in 5 ml of acetonitrile was added at once. The reaction mixture was stirred vigorously during 10 minutes and treated with 5 ml of a saturated solution of sodium sulfite in water. After 1 minute, 5 ml of a saturated solution of sodium carbonate in water were added, and 1 minute latter, 5 ml of a saturated solution of sodium chloride in water were added. The reaction mixture was further stirred during 15 minutes and the suspended solids that formed, were removed by filtration. The filtrate was slowly added to a freshly prepared solution of sodium borohydride (2.5 g, 0.0658 mole) in 60 ml of water. The resulting mixture was stirred vigorously at room temperature during 15 minutes and then treated dropwise with 10 ml of acetone over a period of 10 minutes. The resulting mixture was partitioned between diethyl ether and brine. The ether portion was washed with brine, dried over anhydrous Na₂SO₄ which was then removed by filtration, and evaporated to leave a semi-solid residue. This residue was dissolved in 2 ml of hexane-ethyl acetate (1:1 v:v) solvent and chromatographed on 100 g of silica gel (230-400 mesh ASTM) The 150 ml of hexane-ethyl acetate that were eluted, were evaporated in vacuo to leave 0.575 g (85.4%) of (3aR,6R,7aR)-hexahydro-3,3,6-trimethyl-2-oxide-3H-1,2-benzoxathiole as a semi-solid residue. Further elution of the chromatographic column with 300 ml of hexane-ethyl acetate (43:57 v:v) solvent was done. The solvent was evaporated in vacuo to leave a colorless liquid residue. This liquid was distilled at reduced pressure. The fraction distilling at 55°-60° C. and 0.1 Torr was collected yielding 0.282 g (64.1%) of the title compound, which shows $[\alpha]_{365} = +12.81°$ (C=2.40 in CHCl₃).

Anal. Calcd. for C₇H₁₆O₂: C,63.60; H,12.20; O,24.20. Found: C,63.50; H,12.04; O,24.06.

EXAMPLE 3

Preparation of (2R,4aR,7R,8aR)-hexahydro-1[(2S)-2-hydroxy-2hexanyl]-4,4,7-trimethyl-4H-1,3-benzoxathiin (Compound VII)

A vigorously stirred solution of (4aR,7R,8aR)-hexahydro-4,4, 7-trimethyl-4H-1,3-benzoxathiin (9 g, 0.045 mole, prepared as described by ELIEL et al. Org. Synth. 65, 215 [1987]) in 130 ml of anhydrous tetrahydrofuran was cooled to −78° C. under an argon atmosphere and butyllithium (3.168 g, 0.0495 mole) dissolved in 32 ml of hexane was added dropwise over a period of 15 minutes. The solution was further stirred for additional 15 minutes. The temperature of the solution was allowed to slowly reach 0° C. and further stirred for 15 minutes. The solution was cooled again to −78° C. under the argon atmosphere, the stirring was continued and 2-hexanone (4.5 g, 0.045 mole) dissolved in 25 ml of anhydrous tetrahydrofuran was added dropwise over a period of 20 minutes. The solution was further stirred for additional 4 hours. The temperature of the solution was allowed to slowly reach the room temperature, 10 ml of water were added dropwise over a period of 10 minutes and then 15 ml of a saturated solution of ammonium chloride in water were added at once. The reaction mixture was partitioned between diethyl ether and water. The ether portion was washed with brine, dried over anhydrous Na₂SO₄ which was then removed by filtration, and evaporated to leave 13.1 g of a thick syrup. This thick syrup was dissolved in 10 ml of hexane-ethyl acetate (9:1 v:v) solvent and chromatographed on 1000 g of silica gel (230-400 mesh ASTM). The 5 liters of hexane-ethyl acetate that were eluted, were discarded. Further elution with 3 liters of hexane-ethyl acetate (17:3 v:v) solvent was done. The solvent was evaporated in vacuo to leave a viscous colorless liquid residue. This liquid was distilled at reduced pressure. The fraction distilling at 95°-97° C. and 0.05 Torr was collected yielding 4.7 g (31.8%) of the title compound, which shows $[\alpha]_{365} = -22.35°$ (C=1.91 in CHCl₃)

Anal. Calcd. for C₁₇H₃₂O₂S: C,67.96; H,10.71; O,10.65; S,10.65. Found: C,67.96; H 10.71; O,10.51; S,10.71.

EXAMPLE 4

Preparation of (−)-S-2-methyl-1,2-hexanediol (Compound VI)

Compound VII, prepared above (1 g, 0.00749 mole) was treated as in Example 2, and the product isolated following the procedure therein This yielded 0.284 g (61.5%) of the title compound which shows $[\alpha]_{36} = -12.32°$ (C=2.41 in CHCl₃).

Anal. Calcd. for: C₇H₁₆O₂: C,63.60; H,12.20; O,24.20. Found: C,63.46; H,12.21; O,21.13.

What is claimed is:

1. A process for preparing the optically active compound having Formula I:

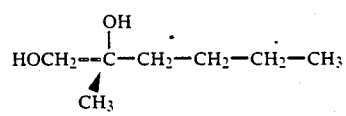

comprising the steps of:
(a) reacting the compound having Formula II:

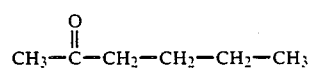

with a compound having Formula III:

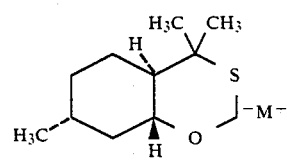

where M+ is an alkali metal cation, in a suitable solvent at temperatures in the range of from about −80° C. to 25° C. and acidifying the solution to produce the compound having Formula IV:

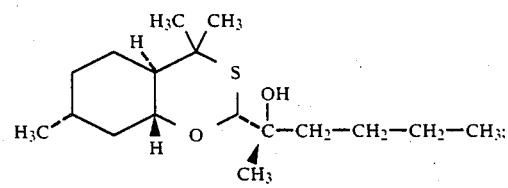

(b) separating Compound IV from the reaction mass;
(c) reacting the compound having Formula IV with an oxidizing agent selected from the group consisting of N-chlorosuccinimide and N-bromosuccinimide in the presence of an inorganic salt selected from the group consisting of silver S nitrate, cadmium nitrate, cupric chloride, mercuric chloride and silver perchlorate in a suitable solvent at temperatures of from about −10° C. to 0° C. to provide the compound having Formula V:

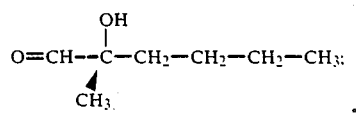

(d) reacting the compound having Formula V with a reducing agent selected from the group consisting of sodium borohydride and lithium borohydride in a suitable solvent at temperature of from about 0° C. to 30° C. to provide the desired compound having Formula I above; and (e) isolating the desired product having Formula I above from the reaction mass.

2. The process of claim 1 wherein the compound having Formula IV is isolated.

3. The process of claim 1 wherein the oxidizing agent is N-chlorosuccinimide.

4. The process of claim 1 wherein the reducing agent is sodium borohydride.

5. The process of claim 1 wherein the inorganic salt is silver nitrate.

6. A process for preparing the optionally active compound having Formula VI:

$$\text{HOCH}_2-\underset{\underset{\text{OH}}{|}}{\overset{\overset{\text{CH}_3}{|}}{C}}-\text{CH}_2-\text{CH}_2-\text{CH}_2-\text{CH}_3 \qquad \text{VI}$$

comprising the steps of:

(a) reacting the compound having Formula II:

$$\text{CH}_3-\overset{\overset{\text{O}}{\|}}{C}-\text{CH}_2-\text{CH}_2-\text{CH}_2-\text{CH}_3 \qquad \text{II}$$

with a compound having Formula III:

III where M+ is an alkali metal cation, in a suitable solvent at temperatures in the range of from about −80° C. to 25° C. and acidifying the solution to produce the compound having Formula VII:

VII (b) separating Compound VII from the reaction mass;

(c) reacting the compound having Formula VII with an oxidizing agent selected from the group consisting of N-chlorosuccinimide and N-bromosuccinimide in the presence of an inorganic salt selected from the group consisting of silver nitrate, cadmium nitrate, cupric chloride, mercuric chloride and silver perchlorate in a suitable solvent at temperatures of from about −10° C. to 0° C. to provide the compound having Formula VIII:

$$\text{O}=\text{CH}-\underset{\underset{\text{OH}}{|}}{\overset{\overset{\text{CH}_3}{|}}{C}}-\text{CH}_2-\text{CH}_2-\text{CH}_2-\text{CH}_3; \qquad \text{VIII}$$

(d) reacting the compound having Formula VIII with a reducing agent selected from the group consisting of sodium borohydride and lithium borohydride in a suitable solvent at temperatures of from about 0° C. to 30° C. to provide the desired compound having Formula VI above; and (e) isolating the desired product having Formula VI above from the reaction mass.

7. The process of claim 6 wherein the compound having Formula VII is isolated.

8. The process of claim 6 wherein the oxidizing agent is N-chlorosuccinimide.

9. The process of claim 6 wherein the reducing agent is sodium borohydride.

10. The process of claim 6 wherein in inorganic salt is silver nitrate.

* * * * *